United States Patent
Furman et al.

(10) Patent No.: US 10,542,927 B2
(45) Date of Patent: Jan. 28, 2020

(54) APPARATUS AND METHOD FOR COMPUTERIZED ROTATIONAL HEAD IMPULSE TEST

(71) Applicants: Neuro Kinetics, Inc., Pittsburgh, PA (US); University of Pittsburgh—Of the Commonwealth System of Higher Education, Pittsburgh, PA (US)

(72) Inventors: Joseph M Furman, Pittsburgh, PA (US); Alexander D Kiderman, Pittsburgh, PA (US); Ian A Shirey, Pittsburgh, PA (US)

(73) Assignees: NEURO KINETICS, INC., Pittsburgh, PA (US); UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 15/596,886

(22) Filed: May 16, 2017

(65) Prior Publication Data
US 2017/0367638 A1  Dec. 28, 2017

Related U.S. Application Data
(60) Provisional application No. 62/337,232, filed on May 16, 2016.

(51) Int. Cl.
*A61B 3/14* (2006.01)
*A61B 3/00* (2006.01)
(Continued)

(52) U.S. Cl.
CPC ............ *A61B 5/4023* (2013.01); *A61B 3/113* (2013.01); *A61B 5/4863* (2013.01);
(Continued)

(58) Field of Classification Search
CPC ..... A61B 3/113; A61B 3/0025; A61B 5/4023; A61B 3/0091; A61B 3/145; A61B 5/4863;
(Continued)

(56) References Cited

U.S. PATENT DOCUMENTS 7,199,471 B2    4/2007  Houston
7,285,099 B1 *  10/2007 Peterka ................ A61B 5/4863
                                                    600/558
(Continued)

OTHER PUBLICATIONS

Macdougall, Hamish G., et al. "Application of the video head impulse test to detect vertical semicircular canal dysfunction." Otology & Neurotology 34.6 (2013): 974-979.
(Continued)

*Primary Examiner* — Brandi N Thomas
(74) *Attorney, Agent, or Firm* — Blynn L. Shideler; Krisanne Shideler; BLK Law Group

(57) ABSTRACT

A system and associated method for computerized rotational head impulse test (crHIT) to assess the semicircular canals of the human vestibular system clinically in patients with balance disorders. The system utilizes a rotary chair combined with a head mounted VOG system with head tracking sensors. The crHIT protocol uses the same physiologic principles as the known video head impulse test (vHIT). The crHIT utilizes whole-body rotation via the chair to yield a persistent controlled, repeatable, comfortable, reliable stimulus can be delivered while recording eye movements with video-oculogaphy.

19 Claims, 5 Drawing Sheets

(51) Int. Cl.
*A61B 5/00* (2006.01)
*A61B 3/113* (2006.01)
*G02F 1/133* (2006.01)
G02F 1/1335 (2006.01)
G01J 1/42 (2006.01)

(52) U.S. Cl.
CPC ........ *G02F 1/13318* (2013.01); *A61B 3/0041* (2013.01); *G01J 1/4228* (2013.01); *G02F 1/133514* (2013.01)

(58) Field of Classification Search
CPC ......... A61B 3/0041; A61B 3/112; A61B 3/02; A61B 5/4076; A61B 5/6803; A61B 3/005; A61B 3/0083; A61B 3/032; A61B 3/11; A61B 5/0496; A61B 5/11; A61B 5/4047; A61B 5/4064; A61B 5/6814; A61B 5/702; A61B 5/7257
USPC ........ 351/200, 205, 206, 209–211, 221, 222, 351/243–246
See application file for complete search history.

(56) References Cited

U.S. PATENT DOCUMENTS

| | | | |
|---|---|---|---|
| 7,448,751 | B2 | 11/2008 | Kiderman et al. |
| 7,520,614 | B2 | 4/2009 | Joos et al. |
| 7,651,224 | B2 | 1/2010 | Wood et al. |
| 7,665,845 | B2 | 2/2010 | Kiderman et al. |
| 7,727,162 | B2 | 6/2010 | Peterka |
| 7,731,360 | B2 | 6/2010 | MacDougall et al. |
| 7,753,523 | B2 | 7/2010 | Kiderman et al. |
| 7,866,818 | B2 | 1/2011 | Schroeder et al. |
| 8,529,463 | B2 | 9/2013 | Della Santina et al. |
| 9,370,302 | B2 | 6/2016 | Krueger |
| 2005/0099601 | A1 | 5/2005 | MacDougall et al. |
| 2006/0082872 | A1* | 4/2006 | Acres ................... G02B 23/18 359/414 |
| 2008/0278665 | A1 | 11/2008 | Uemoto |
| 2011/0028872 | A1* | 2/2011 | Kevin ..................... A61B 5/11 601/86 |
| 2011/0152711 | A1 | 6/2011 | Della Santina et al. |
| 2012/0081666 | A1 | 5/2012 | Kiderman et al. |
| 2014/0314488 | A1 | 10/2014 | Aston et al. |
| 2014/0320817 | A1* | 10/2014 | Kiderman ............. A61B 3/145 351/209 |
| 2014/0327881 | A1 | 11/2014 | Kiderman et al. |
| 2015/0018709 | A1 | 1/2015 | Kiderman et al. |
| 2015/0223683 | A1 | 8/2015 | Davidovics et al. |
| 2015/0335239 | A1 | 11/2015 | Macfougall |
| 2016/0007849 | A1 | 1/2016 | Krueger |
| 2016/0213551 | A1 | 7/2016 | Budagher |
| 2016/0242642 | A1 | 8/2016 | Migliaccio et al. |
| 2016/0262608 | A1 | 9/2016 | Krueger |
| 2016/0270711 | A1 | 9/2016 | Ashmore et al. |
| 2017/0020388 | A1 | 1/2017 | Kiderman et al. |
| 2017/0042462 | A1 | 2/2017 | Kiderman |

OTHER PUBLICATIONS

Macdougall, H. G., et al. "The video head impulse test Diagnostic accuracy in peripheral vestibulopathy." Neurology 73.14 (2009): 1134-1141.
Weber KP, AW ST, Todd MJ, McGarvie LA, Curthoys IS, Halmagyi GM (2008) Head impulse test in unilateral vestibular loss. Neurology, 70: 454-463.
Charles C. Della Santina, Valeria Potyagaylo, Americo A. Migliaccio, Lloyd B. Minor, and John P. Carey, "Orientation of Human Semicircular Canals Measured byThree-Dimensional Multiplanar CT Reconstruction" JARO 6: 191-206 (2005) DOI: 10.1007/s10162-005-0003.
Leigh, J. R. and Zee, D. S. (1999). The Neurology of Eye Movements: Text and CD-ROM: Text and CD-ROM, Oxford University Press, USA.
Goldberg, J. M. and Fernandez, C. (1971). "Physiology of peripheral neurons innervating semicircular canals of the squirrel monkey. I. Resting discharge and response to constant angular accelerations." J Neurophysiol 34(4): 635-660.

* cited by examiner

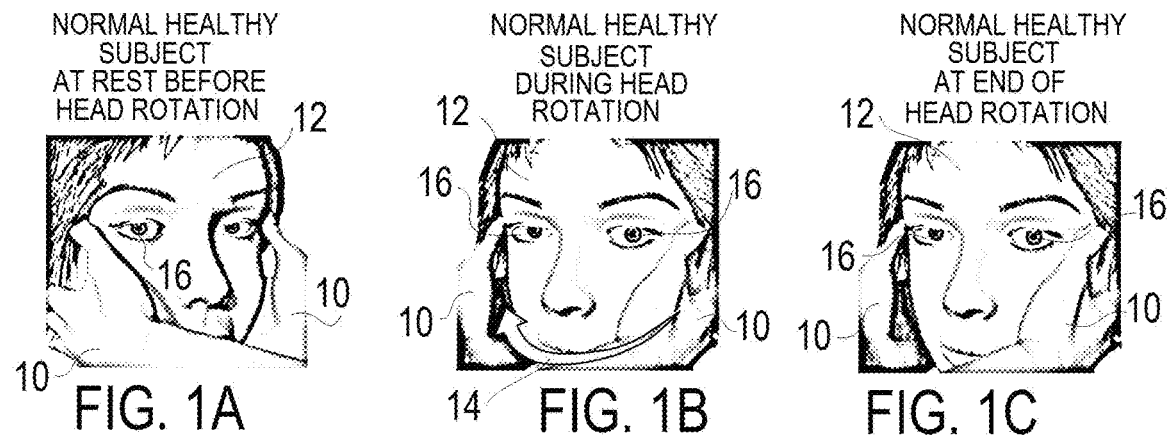
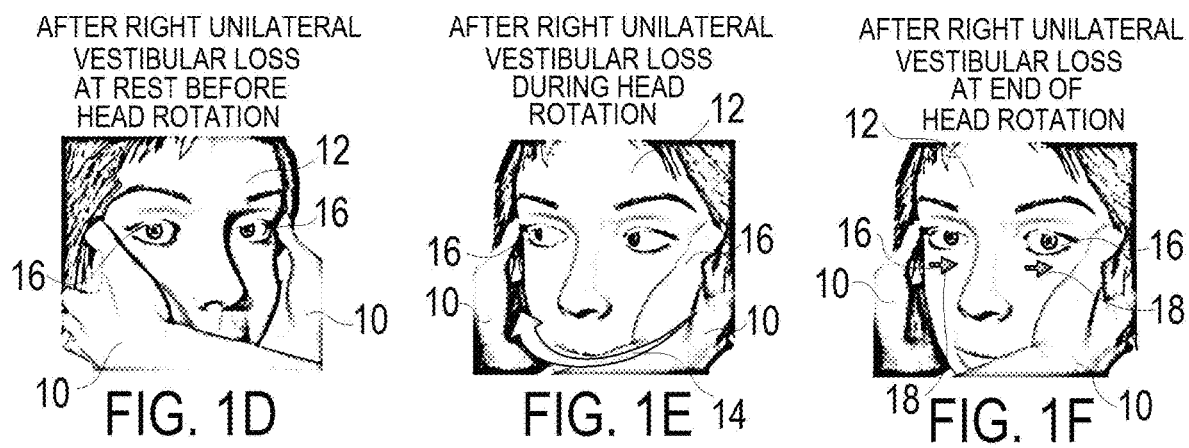
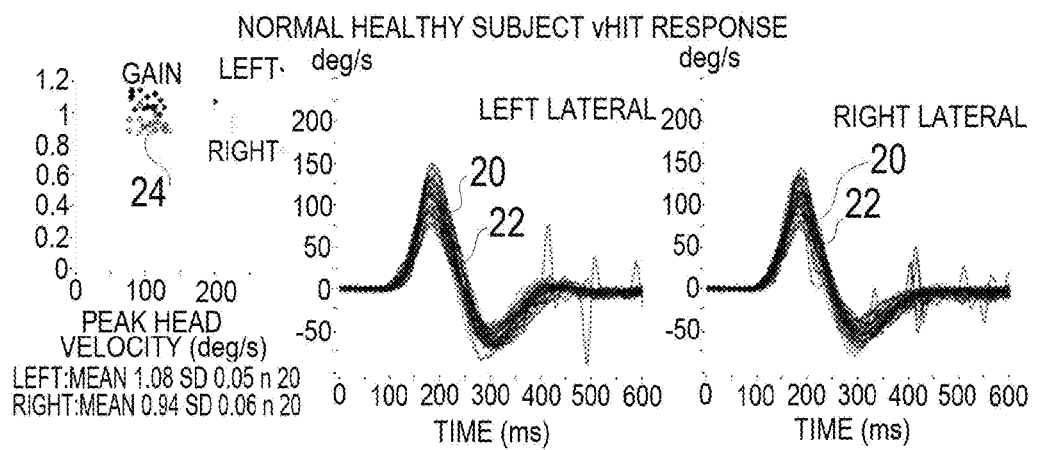
FIG. 2

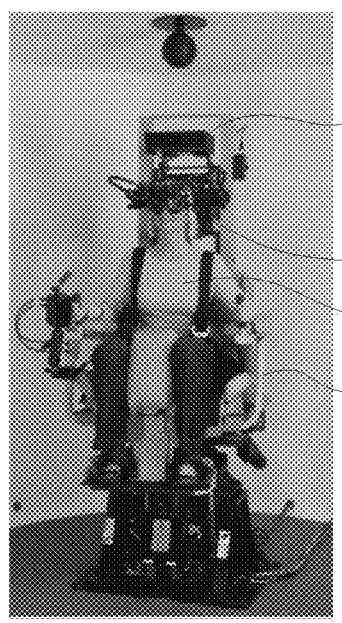
FIG. 5
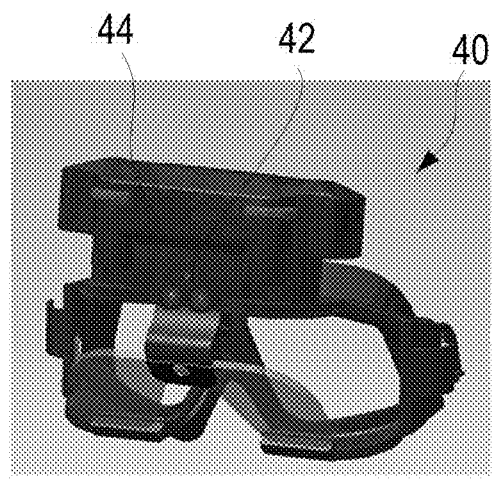
FIG. 6
FIG. 7
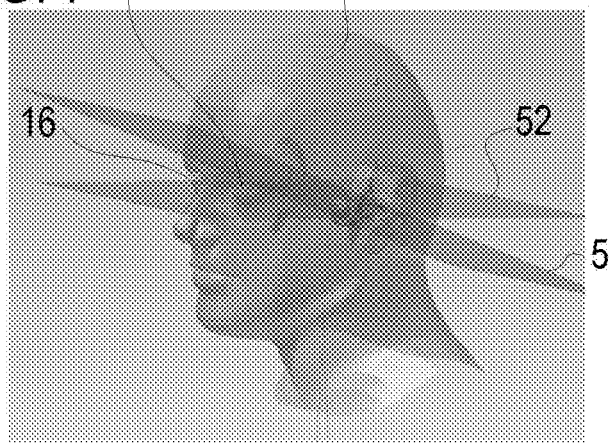
FIG. 8

APPARATUS AND METHOD FOR COMPUTERIZED ROTATIONAL HEAD IMPULSE TEST

RELATED APPLICATIONS

This application claims the benefit of Provisional Application Ser. No. 62/337,232 filed May 16, 2016 entitled "Apparatus and Method for Computerized Rotational Head Impulse Test", which application is incorporated herein by reference.

STATEMENT REGARDING FEDERALLY SPONSORED RESEARCH OR DEVELOPMENT

This invention was advanced with Government support under contract 1R43 DC011984 Computerized Impulsive Rotational Test (CIRT) for Evaluation of Patients with Compensated Vestibular Lesions; and contract 1R43DC014611-01 Computerized Rotational Head Impulse Test-Vertical (CRHIT-Vertical) awarded by National Institute of Health (NIH). Thus this invention was made with government support under grant numbers DC014611 and DC011984 awarded by the National Institutes of Health. The Government has certain rights in the invention.

BACKGROUND OF THE INVENTION

Field of the Invention

The present invention pertains to a system and method for assessing the semicircular canals of the human vestibular system, and more particularly to an objective head impulse test.

Background Information

Head Impulse Test

The Head Impulse Test (HIT) is a widely used clinical assessment technique used to assess the angular vestibulo-ocular reflex (aVOR).

Specifically, the traditional HIT assesses horizontal semicircular canal (HSCC) and superior vestibular nerve function in response to discrete, small amplitude (~10°), high acceleration (~3000-4000°$s^2$) rotational head impulses. For ease of understanding normal conventional results are shown in FIGS. 1A-C and abnormal results are shown in FIGS. 1D-F During the HIT, clinician 10 stands before the patient 12, holding the patient's head in his hands, and the patient 12, who is typically looking straight at the clinician 10, is asked to keep their eyes 16 staring at the earth fixed target (e.g., the clinician's nose). The examiner or clinician 10 will then manually generate a rapid head impulse 14 (schematically shown in FIGS. 1 B and 1E) while monitoring the patient's eyes 16 for a corrective or compensatory saccade (CS) response or "overt saccade" (OS) (collectively shown at 18 in FIG. 1F) which is a rapid eye movement 18 generated by the brain to re-fixate the patient's eyes 16 on the intended target if the aVOR is unable to generate an adequate slow phase eye movement due to peripheral weakness or loss on ipsi-rotational side. Individuals 12 with normal vestibular function should not generate a CS/OS 18 after a head impulse 14, in other words the eyes 16 should stay fixed on the target throughout the impulse 14 movement. People 12 with vestibular hypofunction may generate a corrective or overt saccade 18 after the head is quickly rotated via impulse 14 toward the affected (pathological) side and this is considered a (+) HIT.

It is worth reiterating that in conventional HIT, if the patient's vestibulo-ocular response is inadequate then their eyes 16 will be taken off target during the head rotation 14 as shown in FIG. 1E, because their eyes 16 will not rotate at the correct speed to exactly compensate for head rotation 14. So an inadequate VOR means that the eyes 16 go with the head of the individual 12 during the passive unpredictable head turn via impulse movement 14 and will be taken off target by the head turn 14, so that at the end of the head turn 14 the patient 12 must make a corrective saccade 18 back to the target such as the clinician's nose. To the clinician 10 watching the patient's eyes 16, this corrective or overt saccade 18 is usually very clear (yielding the phrase an overt saccade). The corrective or overt saccade 18 in HIT is the telltale sign of inadequate semicircular canal function on the side to which the head was rotated via impulse 14. So an overt saccade 18 after a leftwards head rotation means the left semicircular canal has a deficit. If there is any doubt, the clinician 10 just repeats the head impulses 14 until they are satisfied.

This clinical 10 test takes advantage of Ewald's Second Law. Ernst Julius Richard Ewald (14 Feb. 1855-22 Jul. 1921) was a German physiologist best remembered for his research of the vestibular system of the inner ear, that largely involved experiments performed on the semicircular canal system of pigeons. From these studies the so-called "Ewald laws" are derived, which deal with the effects of endolymph motion on body, head and eye movements and also on the phenomena of excitation-inhibition asymmetries in the vestibular system: Ewald's first law: "The axis of nystagmus parallels the anatomic axis of the semicircular canal that generated it"; and Ewald's second law: "Ampullopetal endolymphatic flow produces a stronger response than ampullofugal flow in the horizontal canal". Ewald's Second Law in relation to HIT suggests that for a given impulse 14 in the plane of the HSCCs, a head movement generates a larger magnitude vestibular stimulus on the side to which the impulse 14 was directed (i.e, ipsi-rotational) than it does on the contra-rotational side (opposite the direction of the head impulse). Stated another way, excitation is a stronger vestibular stimulus than is inhibition (See Leigh, J. R. and Zee, D. S. (1999). The Neurology of Eye Movements: Text and CD-ROM: Text and CD-ROM, Oxford University Press, USA.). Ewald's second law is thought to be due to the inability of inhibitory stimuli to decrease vestibular nerve firing rates to less than zero (see Goldberg, J. M. and Fernandez, C. (1971). "Physiology of peripheral neurons innervating semicircular canals of the squirrel monkey. I. Resting discharge and response to constant angular accelerations." J Neurophysiol 34(4): 635-660.). In persons 12 with intact vestibular function, vestibular nerve firing frequencies are able to increase in accordance with increasing ipsi-rotational velocities or accelerations without saturating or requiring a compensatory saccade 18 to stabilize gaze.

The traditional manual clinical HIT is not scored per se, aVOR function is evaluated as normal or abnormal (i.e., hypofunctional) by noting the presence (+ finding) or absence (− finding) of a compensatory or overt saccade.

Objective Head Impulse Test

The subjective nature of visually observing the conventional HIT lead to objective platforms for this testing, including the use of scleral search coils for measurement of eye 16 movement in HIT protocols (See Weber K P, Aw S T, Todd M J, McGarvie L A, Curthoys I S, Halmagyi G M (2008) Head impulse test in unilateral vestibular loss. Neurology, 70: 454-463. The scleral search coil method of measuring eye movement in HIT achieves the aim of objective eye measurement in HIT, but it is clinically unrealistic, because of its huge expense, the high cost of each coil, the complexity of processing the data and the fact that patients 12 do not like having a contact lens placed on their eyes 16.

In addition to objective eye movement data with scleral search coils in HIT protocols, such objective and precise measurement systems showed that some patients 12 with a semicircular canal deficit on one side could manage to generate small corrective saccades actually during the head movement at impulse 14, so that at the end of the head turn to their affected side hardly any overt saccades 18 were necessary to bring the eyes 16 back on target. These small "hidden" saccades during the head rotation via impulse 14 had acted to conceal the subjects inadequate VOR. Thus these hidden or covert saccades can entirely obscure or conceal even a complete, total loss of canal function. These hidden or covert saccades are very fast and they occur during the head rotation 14 and thus they can be almost impossible to detect by the clinician's naked eye and are thus only observable with objective head impulse systems using precise eye measurements.

In addition to scleral search coil method of measuring eye movement in HIT others have used video eye tracking systems 40 also called VOG systems, such as the I-Portal® system from Neurokinetics, Inc. (NKI) in Pittsburgh, in HIT protocols. The details of video eye tracking or VOG systems 40 in general are found in U.S. Patent Publication Numbers 2017-0042462, 2017-0020388, 2016-0270711, 2015-0018709; 2014-0-327881, 2014-0320817, 2014-0314488, 2012-0081666, 2008-0278665, and 2005-0099601 which are incorporated herein by reference. HIT testing performed with VOG systems 40 is sometimes called video head impulse test (vHIT) See MacDougall, H. G., et al. "The video head impulse test Diagnostic accuracy in peripheral vestibulopathy." *Neurology* 73.14 (2009): 1134-1141. The vHIT protocol does measure eye 16 velocity and does detect covert or hidden saccades and is non-invasive and is practical in clinics. In vHIT protocols a small sensor 44 on the goggles 40 measures the head movement (in FIG. 6 the sensor 44 is shown mounted within the housing for the optical components of the goggle system 40, although the sensor can be placed anywhere in the system 40. The whole goggle system 40 is lightweight but it must be secured tightly to the head of the patient 12 to minimize goggle slippage, because any slippage of the goggles 40 will move the camera relative to the eye and so be registered as a movement of the eye and thus generate artifacts (erroneous or noisy data). Google 40 slippage will also generate head movement measurement artifacts as the sensor 44 is measuring the goggle movement, which with goggle slippage is different from the head movement.

The vHIT yields more objective results for detailed analyses as noted in FIG. 2 in which head rotation speed 20 from an impulse or movement 14 and eye movement speed 22 are graphed together and the ratio 24 of the peak velocities thereof forms the objective gain measurement. FIG. 3 illustrates the vHIT protocol results for a patient 12 with bilateral vestibular loss. FIG. 4 illustrates the vHIT protocol results for a patient 12 with unilateral vestibular loss. Additionally, vHIT has been proposed for assessing vertical canals as explained further in MacDougall, Hamish G., et al. "Application of the video head impulse test to detect vertical semicircular canal dysfunction." *Otology & Neurotology* 34.6 (2013): 974-979, however the system and associated method disclosed herein fails to isolate the canal and creates substantial problems in the assessment protocol. Additionally there is the inherent limit of "head only" rotation and the associated physiologic constraints associated therewith It is an object of the present invention to overcome the deficiencies of the prior art and to provide an objective system and method for assessing the semicircular canals of the human vestibular system.

SUMMARY OF THE INVENTION

The object of the present invention is achieved according to one embodiment of the present invention by providing a system and associated method for computerized rotational head impulse test (crHIT) to assess the semicircular canals of the human vestibular system clinically in patients with balance disorders. The system utilizes a rotary chair combined with a head mounted VOG system with head tracking sensors. The crHIT protocol uses the same physiologic principles as the known video head impulse test (vHIT). The crHIT utilizes whole-body rotation via the chair to yield a persistent controlled, repeatable, comfortable, reliable stimulus can be delivered while recording eye movements with video-oculography. The use of the crHIT to assess the horizontal and vertical semicircular canals is an improvement upon an existing useful clinical methodology. The term computerized herein reflects the impulse is automated and does not rely upon manual impulses or movements.

Further, the use of the crHIT to assess the vertical semicircular canals is especially significant and vertical crHIT has the potential to become a widely-used indispensable method of assessing the vertical semicircular canals, which represent a full 40% of inner ear balance function currently not assessable by any reliable method.

The crHIT protocol of the present system and method will enable assessment of all six semicircular canals of the human vestibular system. This techniques will be of great importance in the assessment of patients with dizziness and disequilibrium.

One aspect of the invention provides a method for computerized rotational head impulse testing of a subject comprising the steps of: providing a system for assessing at least one pair of the semicircular canals of the human vestibular system including a rotary chair having controllable rotary motion, a head mounted VOG system with head tracking sensors and a target generation system; placing the a head mounted VOG system with head tracking sensors on the subject whereby the VOG system tracks and records eye movement from the subject; placing the subject into the chair; generating a visual target for the subject with the target generation system; generating at least one head impulse for the subject via whole body rotation of the subject in the chair through controlled rotation of the chair; and recording eye movements and head movements by the head mounted VOG system with head tracking sensors. Tracking of eye movements and head movements includes tracking position, velocity and acceleration of the associated movement.

The method for computerized rotational head impulse testing of a subject according to one aspect of the invention provides wherein the controlled rotation of the chair is through a servo motor control with high resolution encoder. The method according to one aspect of the invention further includes the step of fore-aft adjusting of the subject in the chair to place the subject on a desired vertical axis for testing. The method according to one aspect of the invention wherein the chair further includes a fiber optic slip ring which passes data from the VOG system and wherein the VOG system is operating at least at 250 FPS. The method according to one aspect of the invention provides that the head tracking sensors of the VOG system are 6 degrees of freedom sensors and includes a calibration laser installed on the VOG system. The method according to one aspect of the invention provides wherein the target generation system is a laser based system mounted on the chair.

The method for computerized rotational head impulse testing of a subject according to one aspect of the invention further includes the step of calibrating the head tracking sensor of the head mounted VOG system to the orientation of the subjects canals whereby a transformation matrix can be used to transform movement data to the specific canals. The method according to one aspect of the invention includes the step of assessing of at least the vertical semicircular canals of the subject with the recording of the eye movements and head movements by the head mounted VOG system with head tracking sensors and in another aspect includes the step of assessing of all six semicircular canals of the subject with the recording of the eye movements and head movements by the head mounted VOG system with head tracking sensors.

The method for computerized rotational head impulse testing of a subject according to one aspect of the invention provides wherein the controlled rotation of the chair includes rotating the chair in an oscillating fashion at low amplitude less than +/−15 degrees and at a frequency between 0.1 and 0.3 Hz and in another aspect of the invention the controlled rotation of the chair includes rotating the chair in random directions for at 750 to 1000 deg/sec$^2$ chair acceleration.

The method for computerized rotational head impulse testing of a subject according to one aspect of the invention further includes the step of placing the patient in proper orientation to align either the RALP or LARP canals in an earth-horizontal plane, and wherein the step of placing the patient in proper orientation to align either the RALP or LARP canals in an earth-horizontal plane comprising aligning a head mounted goggle laser image with an image generated by the visual stimulus generating system.

One aspect of the invention provides a method for computerized rotational head impulse testing of a subject comprising the steps of: a) providing a system for assessing the semicircular canals of the subject including a rotary chair having controllable rotary motion and a head mounted VOG system with head tracking sensors; b) placing the a head mounted VOG system with head tracking sensors on the subject whereby the VOG system tracks and records eye movement from the subject; c) placing the subject into the chair; d) placing the patient in proper orientation to align either the horizontal, RALP or LARP canals in an earth-horizontal plane; e) generating at least one head impulse for the subject via whole body rotation of the subject in the chair through controlled rotation of the chair; f) recording eye movements and head movements by the head mounted VOG system with head tracking sensors; g) repeating steps D-F for the remaining canals; and h) assessing of all six semicircular canals of the subject with the recording of the eye movements and head movements by the head mounted VOG system with head tracking sensors.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

The features that characterize the present invention are pointed out with particularity in the claims which are part of this disclosure. These and other features of the invention, its operating advantages and the specific objects obtained by its use will be more fully understood from the following detailed description and the operating examples.

DESCRIPTION OF THE FIGURES

FIGS. 1A-C schematically illustrate a head impulse test for a normal subject;

FIGS. 1D-F schematically illustrate a head impulse test for a subject with inadequate vestibulo-ocular response;

FIG. 2 schematically illustrates head impulse test results using an eye tracking system with head motion tracking such as in vHIT protocols in which head rotation speed and eye movement speed are graphed together;

FIG. 5 schematically illustrates a Computerized Rotational Head Impulse Test (Crhit) System according to one aspect of the present invention;

FIG. 6 schematically illustrates a head mounted goggle based VOG system for use in the Crhit system of the present invention;

FIG. 7 schematically illustrates the orientation planes of semicircular canals vs. human skull landmarks of a subject;

FIG. 8 illustrates a calibration verification screen for calibration of sensors of the Crhit system to the orientation of the user canals;

DESCRIPTION OF THE PREFERRED EMBODIMENTS

Figure 3:
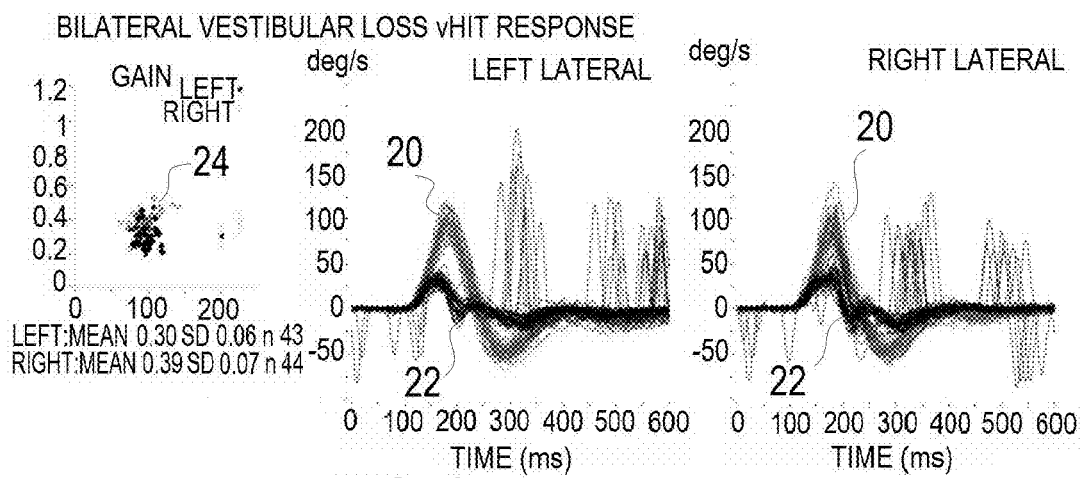
FIG. 3 schematically illustrates the vHIT protocol results for a subject 12 with bilateral vestibular loss.
Figure 4:
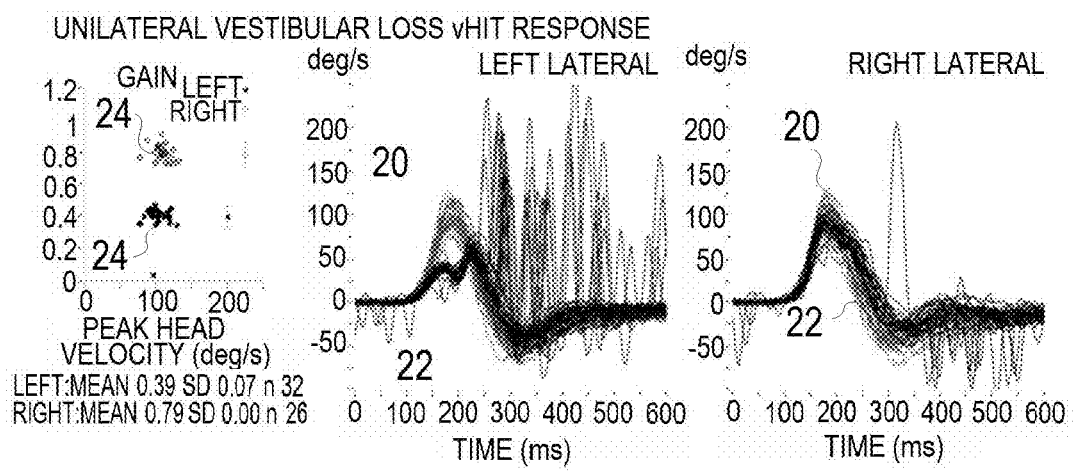
FIG. 4 schematically illustrates the vHIT protocol results for a subject with unilateral vestibular loss.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other. The phrase "slide flute type" will reference "continuous pitch wind instruments" and the phrases may be effectively used interchangeably herein.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Computerized Rotational Head Impulse Test (Crhit) System

FIG. 5 illustrates a Computerized Rotational Head Impulse Test (Crhit) System according to one aspect of the present invention. The system utilizes a rotary chair 30 for repeatable motion, such as included with the I-PORTAL® Neuro-Otologic Test Center from NKI. The chair 30 is shown in FIG. 5 and is designed for maximum patient comfort. The chair includes a precise drive that provides accurate patient testing with minimal vibration, such a drive motor is described in U.S. Pat. No. 7,199,471, which is incorporated herein by reference. Preferably a servo motor control with high resolution encoder creates precise motion profiles. The chair 30 may include a fiber optic slip ring which passes noise free eye data from the VOG goggle system. The chair 30 is preferably adjustable fore-aft position to place patient on axis for accurate and comfortable testing.

The chair 30 is combined with a head mounted goggle based VOG system 40, such as the I-Portal® VOG system from NKI, preferably a high speed system (High speed Goggle operating at 250 FPS or higher). The details of the VOG system 40 are also disclosed in U.S. Pat. Nos. 7,448, 751; 7,520,614; 7,651,224; 7,665,845; 7,731,360; 7,753, 523; and 7,866,818, which are incorporated herein by reference. An appropriate VOG system 40 is shown in FIG. 5 on a patient 12 with the chair and in isolation in FIG. 6. The VOG System 40 has built in 6 degrees of freedom sensor (6 DOF) and a calibration laser 42 installed at the center of goggle system 40.

The system of the invention also uses a visual stimulus generating system 50 such as a laser, which can be the Pursuit Tracker @ laser from NKI. The visual stimulus generating system 50 is described in greater detail in U.S. Pat. No. 8,333,472 which is incorporated herein by reference.

The chair 30, goggle based VOG system 40 (including the position sensors 44) and visual stimulus generating system 50 can be controlled by and send data to a common control computer run by the clinician 10.

Computerized Rotational Head Impulse Test (crHIT) Method

The crHIT protocol of the invention not only isolates and tests horizontal canals but also Anterior and Posterior semicircular canals: known as the Left Anterior Right Posterior (LARP) canals; and Right Anterior, Left Posterior (RALP) canals. The orientation 52 of semicircular canals vs. human skull landmarks of a patient 12 are schematically shown in FIG. 7 and is already known and described in Charles C. Della santina, Valeria Potyagaylo, Americo A. Migliaccio, Lloyd B. Minor, and John P. Carey, "Orientation of Human Semicircular Canals Measured by Three-Dimensional Multiplanar CT Reconstruction" JARO 6: 191-206 (2005) DOI: 10.1007/s10162-005-0003).

The first step of the crHIT methodology is calibrating the head mounted goggle 40 of the subject 12 to the orientation 52 of the subjects canals (the Yaw, Pitch and roll axis of the patients canals). The 6 degrees of freedom sensor (6DOF) 44 installed into goggle system 40 is at a known position to the relative positional frame of the goggle system 40. Once the goggle system 40 and the associated sensors 44 are calibrated to the specific individual 12 a transformation matrix can be used to transform movement data to the specific canals.

For calibration of sensors 44 to the Roll and yaw axes of the patient 12: the patient 12 is instructed to move his head (with goggle system 40 in place) in sync with a target generated by visual stimulus generating system 50 moving vertically while recordings are taken from sensor array 44 The laser 42 on the goggle system 40 can be used to easily align and verify these movements as the patient 10 merely needs to match or align the image of the laser from laser 42 with target image from the visual stimulus generating system 50. Based upon this known vertical movement system generates proposed roll and yaw transform matrix 54 (only one of which is displayed in FIG. 8. The clinician 10 has only to except results by clicking accept roll and pitch buttons 56 during this calibration assuming he verifies the subject 12 matched the desired calibration movement. For calibration of the pitch axis and generation of a pitch transform matrix 54 the clinician 10 manually moves the head of the patient 12 until Reid's plane is earth-horizontal and the system takes a reading of the pitch angle of the sensor array 44 by having the system except and save data via a simple input at 56 by the clinician 10.

Following the calibration, using available matrix location of vertical canals in space, the 6 DOF sensor 44 outputs is transferred to patient's vestibular canals orientation. After this transformation, outputs of 6 DOF (3 gyros) are define motion input to all Semicircular Canals.

Another calibration step is the calibration of patient 10 and the goggles 40: With patient 10 upright, the system 40 calibrates horizontal and vertical eye movement of the eyes 16. This calibration is known for VOG systems 40 in general.

Figure 9:
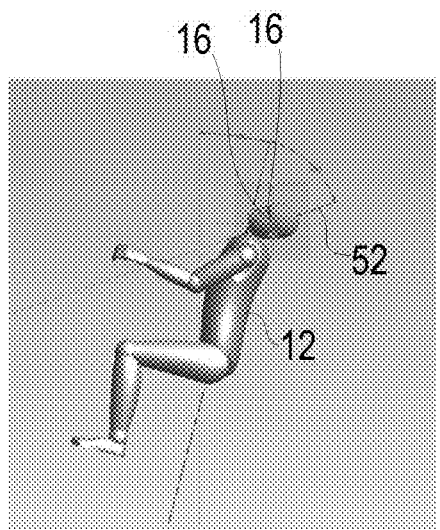
FIG. 9 schematically illustrates the position of a subject for testing of the LARP canals with LARP isolation.
Figure 10:
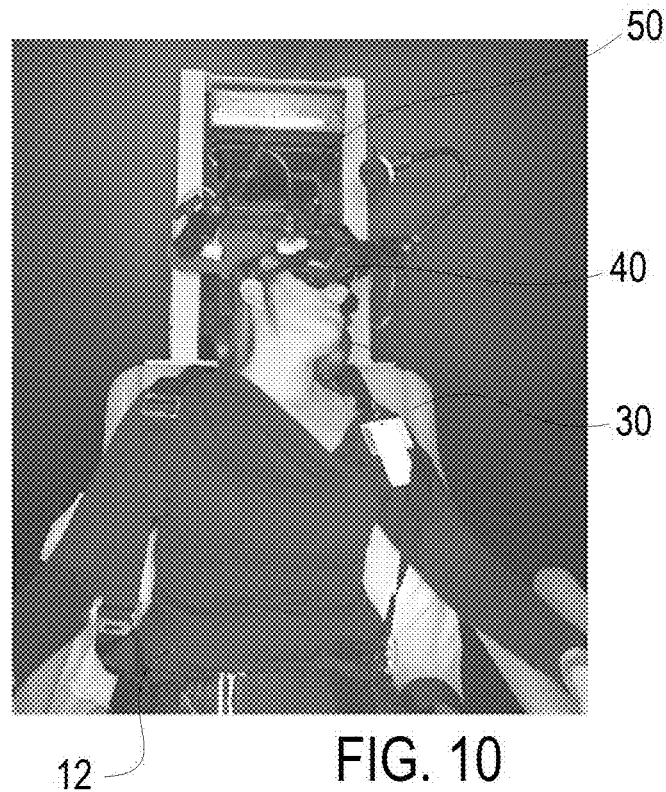
FIG. 10 illustrates the position of a subject in the Crhit system for testing of the LARP canals with LARP isolation.

With the system calibrated the clinician 10 can place patient 12 in proper orientation to align either Horizontal, RALP or LARP canals in the earth-horizontal plane. The horizontal position for the patient 12 is simple and is well known, and FIG. 9 shows schematically the position of the subject 10 for testing of the LARP canals and FIG. 10 illustrates the position of the subject 10 for testing of the LARP canals with the chair 30 and goggles 40 and stimulus generation system 50.

Figure 11:
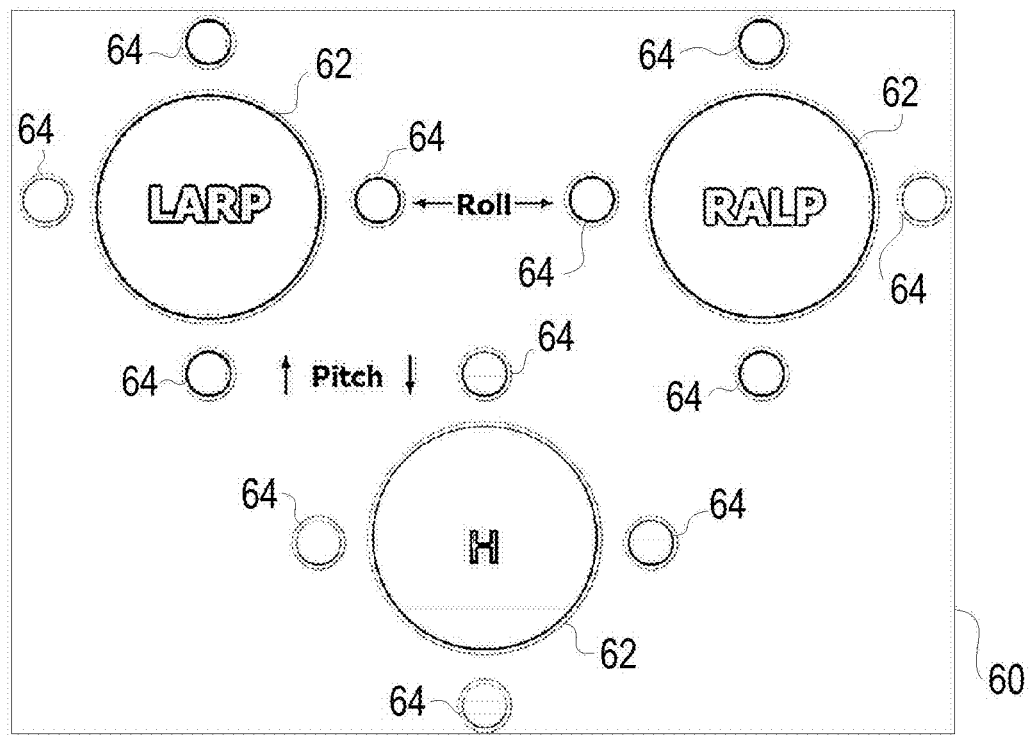
FIG. 11 schematically illustrates a positioning guide visible to the clinician 10 for facilitating the positioning and isolation of the Horizontal, RALP or LARP canals of a subject.

The software can include a positioning guide 60 on the control computer visible to the clinician 10 whereby as soon as Horizontal, RALP or LARP canals in correct position, an appropriate circle (LARP, RALP or HORIZONTAL 62) on a positioning screen 60 will illuminate. A representative positioning screen is shown in FIG. 11. The positioning screen 60 can also include reference circles 64 (specifically 4 reference circles, one above, one below, one left and one right of an associated circle 62) that will be selectively highlighted to illustrate the relative position of the current canal relative to horizontal plane. The reference circles 64 can be used to guide or advise the clinician 10 which direction to move the head of the patient 12 to align the desired canal to horizontal.

With the patients head and eyes 16 in the desired position to isolate one of the pairs of canals (i.e. to align one of the pairs of canals with the rotary movement of the chair) a fixed stimulus is generated by the visual stimulus generating system 50 in a location appropriate for the current position of the subjects head. In practice the goggle laser 42 is on during positioning of the patient 10 and with the patient eyes 16 in the desired position the clinician 10 aligns the goggle laser 42 with the visual stimulus generating system laser 50 image to form the target and the goggle laser 42 is turned off for the test.

The subject is told to look at the now stationary target laser from system 50 and the chair 30 may be rotated in an oscillating fashion at low amplitude (not more than +/−15 degrees), mid-frequency (0.1-0.3 Hz) or higher frequencies and amplitudes and will always yield a repeatable accurate head impulse 14. The system can be used to record eye position 22 and calculate VOR gain during the head impulse 14 (VOR gain should be approximately 1 for healthy individuals). Preferably the system uses random directions for the at 750 to 1000 deg/sec$^2$ chair acceleration, and records sensor outputs in all three axes and horizontal, vertical and torsion left and right eyes positions.

Figure 12:
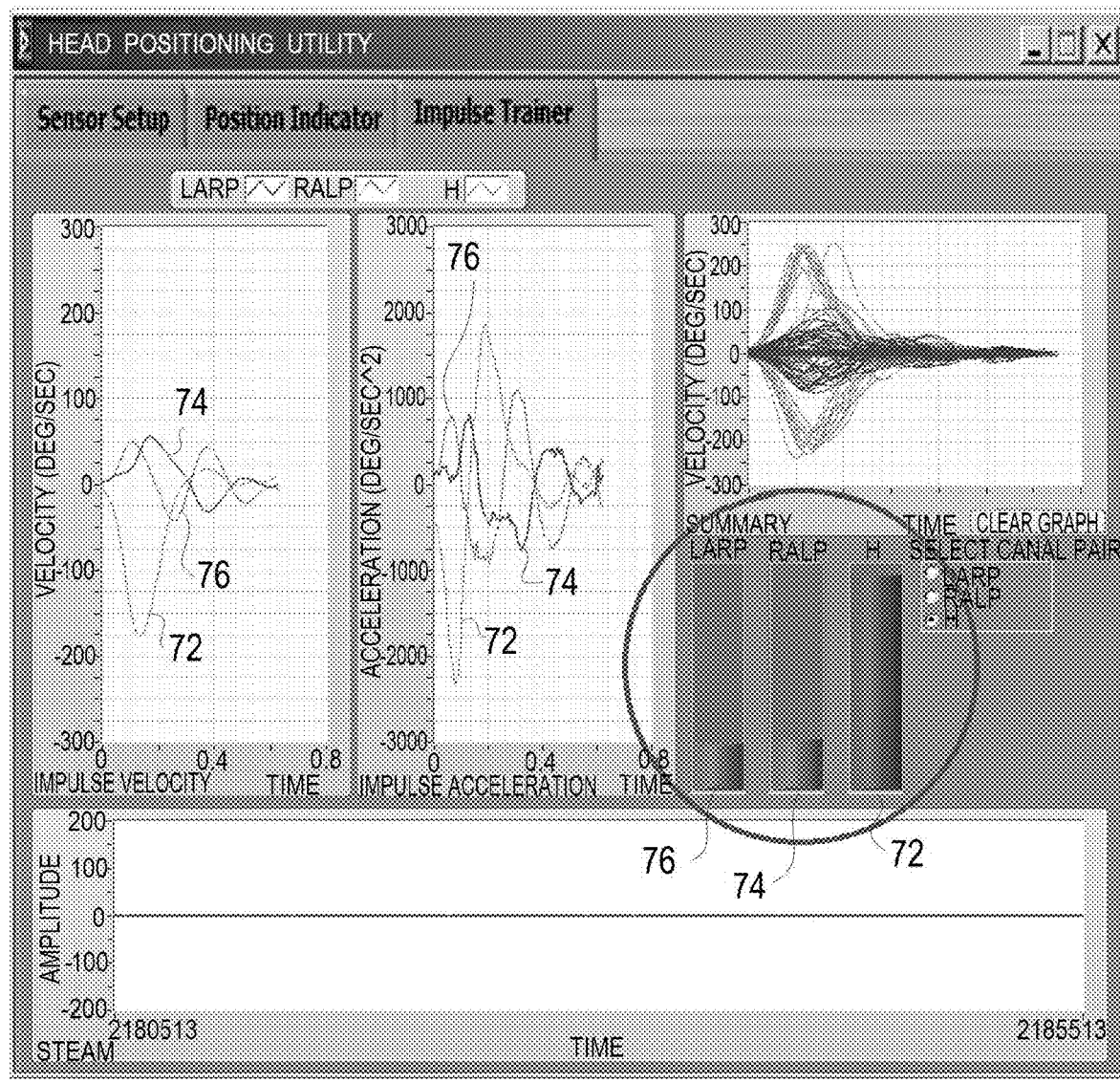
FIG. 12 is a screenshot illustrating the degree of horizontal canal isolation compared with degree of motion of the RALP and the LARP canal motion, with graphs showing the relative motion (velocity and acceleration) of each canal during the motion.

The system can confirm that axis of rotation (earth-vertical) is perpendicular to either desired horizontal canal pair, the RALP canal pair or LARP canal pair plane and can document the level of canal isolation as shown in FIG. 12. Specifically FIG. 12 shows the degree of horizontal canal isolation 72 compared with degree of motion of the RALP 74 and the LARP canal 76, with graphs showing the relative motion (velocity and acceleration) of each canal during the motion. It should be identified that the complete isolation of the distinct canals is not required merely the substantial isolation as shown, with substantial isolation being movements of the isolated canal having velocity and acceleration more than twice that of the remaining canals and typically 3 or 4 times greater or more. The process can be repeated for each canal pair.

For analysis, use the component of the rotation axis onto the transformed pitch rotation axis, i.e., the pitch axis in Reid's plane, as the stimulus and use vertical eye position as the response. Compute gain using the same methods as those used for horizontal crHIT.

The subject 12 need only maintain their head in the fixed position as the impulse 14 is via chair 30 rotation. Further the system can confirm the subject 12 is maintaining their head in the desired orientation and can provide audio or visual feedback to the clinician 10 when the patient 12 moves outside of preset thresholds relative to a given canal which may invalidate the data.

As noted above the present invention provides a system and associated method for computerized rotational head impulse test (crHIT) to assess the semicircular canals of the human vestibular system clinically in patients with balance disorders. The system utilizes a rotary chair 30 combined with a head mounted VOG system 40 with integral head tracking sensors 44 and a target generation system 50. The crHIT protocol uses the same physiologic principles as the known video head impulse test (vHIT). The crHIT utilizes whole-body rotation via the chair 30 to yield a persistent controlled, repeatable, comfortable, reliable stimulus or impulse 14 which can be delivered while recording eye movements of the eyes 16 of the subject 12 with video-oculogaphy. The use of the crHIT to assess the horizontal semicircular canals is an improvement upon an existing clinical methodology. Further, the use of the crHIT to assess the vertical semicircular canals is especially significant and vertical crHIT has the potential to become a widely-used indispensable method of assessing the vertical semicircular canals, which represent a full 40% of inner ear balance function currently not assessable by any reliable method.

The crHIT protocol of the present system and method will enable assessment of all six semicircular canals of the human vestibular system. This techniques will be of great importance in the assessment of patients 10 with dizziness and disequilibrium.

Position Indicator for vHIT

Using only the goggles 40 with sensors 44 and a visual indicator 60 in the associated control laptop, the present invention provides a position indicator for improved vHIT. The present invention could be utilized without the chair 30 in vHIT protocols and the invention, based on the Transformation matrix between the sensors 44 and the canals of the user 12 (angular velocity of Horizontal, Anterior and Posterior semicircular canals) the system creates "Position Indicator" that allow clinicians to run proper canals evaluation in vHIT. Namely once the patients head is in the proper position the HIT protocol can be performed on isolated canals using small manually induced motions about a vertical axis. The system can verify that the motion is maintained in the proper plane via the sensors 44 and this can be graphically shown as noted above. One difficulty here is that the range of motion of the subject becomes very limited when coupled with the isolation positioning (which is not an issue when using the chair with the crHIT protocol above)

The embodiments of the invention discussed above are merely representative of the present invention. Various changes may be made to the present invention without departing from the spirit and scope thereof. The scope of the present invention is defined by the appended claims and equivalents thereto.

What is claimed is:

1. A method for computerized rotational head impulse testing of a subject comprising the steps of:
    providing a system for assessing at least one pair of the semicircular canals of the subject including a rotary chair having controllable rotary motion, a head mounted VOG system with head tracking sensors and a target generation system;
    placing the a head mounted VOG system with head tracking sensors on the subject whereby the VOG system tracks and records eye movement from the subject;
    placing the subject into the chair;
    generating a visual target for the subject with the target generation system;
    generating at least one head impulse for the subject for rotational head impulse testing of a subject via whole body rotation of the subject in the chair through controlled rotation of the chair;
    recording eye movements and head movements by the head mounted VOG system with head tracking sensors and
    analyzing the results including isolating and assessing at least one pair of the semicircular canals of the subject.

2. The method for computerized rotational head impulse testing of a subject according to claim 1 wherein the controlled rotation of the chair is through a servo motor control with high resolution encoder.

3. The method for computerized rotational head impulse testing of a subject according to claim 1 further including the step of fore-aft adjusting of the subject in the chair to place the subject on a desired vertical axis for testing.

4. The method for computerized rotational head impulse testing of a subject according to claim 1 wherein the chair further includes a fiber optic slip ring which passes data from the VOG system.

5. The method for computerized rotational head impulse testing of a subject according to claim 1 wherein the VOG system is operating at least at 250 FPS.

6. The method for computerized rotational head impulse testing of a subject according to claim 1 wherein the head tracking sensors of the VOG system are 6 degrees of freedom sensors.

7. The method for computerized rotational head impulse testing of a subject according to claim 1 further including a calibration laser installed on the VOG system.

8. The method for computerized rotational head impulse testing of a subject according to claim 1 wherein the target generation system is a laser based system mounted on the chair.

9. The method for computerized rotational head impulse testing of a subject according to claim 1 further including the step of calibrating the head tracking sensor of the head mounted VOG system to the orientation of the subjects canals whereby a transformation matrix can be used to transform movement data to the specific canals.

10. The method for computerized rotational head impulse testing of a subject according to claim 1 including the step of assessing of at least the vertical semicircular canals of the subject with the recording of the eye movements and head movements by the head mounted VOG system with head tracking sensors.

11. The method for computerized rotational head impulse testing of a subject according to claim 1 including the step of assessing of all six semicircular canals of the subject with the recording of the eye movements and head movements by the head mounted VOG system with head tracking sensors.

12. The method for computerized rotational head impulse testing of a subject according to claim 1 wherein the controlled rotation of the chair includes rotating the chair in an oscillating fashion at low amplitude less than +/−15 degrees and at a frequency between 0.1 and 0.3 Hz.

13. The method for computerized rotational head impulse testing of a subject according to claim 1 wherein the controlled rotation of the chair includes rotating the chair in random directions for at 750 to 1000 deg/sec.sup.2 chair acceleration.

14. The method for computerized rotational head impulse testing of a subject according to claim 1 further including the step of placing the patient in proper orientation to align either the RALP or LARP canals in an earth-horizontal plane.

15. The method for computerized rotational head impulse testing of a subject according to claim 14 wherein the step of placing the patient in proper orientation to align either the RALP or LARP canals in an earth-horizontal plane comprising aligning a head mounted goggle laser image with an image generated by the visual stimulus generating system.

16. A method for computerized rotational head impulse testing of a subject comprising the steps of:
A) providing a system for assessing the semicircular canals of the subject including a rotary chair having controllable rotary motion and a head mounted VOG system with head tracking sensors;
B) placing the a head mounted VOG system with head tracking sensors on the subject whereby the VOG system tracks and records eye movement from the subject;
C) placing the subject into the chair;
D) placing the patient in proper orientation to align either the horizontal, RALP or LARP canals in an earth-horizontal plane;
E) generating at least one head impulse for the subject via whole body rotation of the subject in the chair through controlled rotation of the chair;
F) recording eye movements and head movements by the head mounted VOG system with head tracking sensors;
G) Repeating steps D-F for the remaining canals; and
H) assessing of all six semicircular canals of the subject with the recording of the eye movements and head movements by the head mounted VOG system with head tracking sensors.

17. The method for computerized rotational head impulse testing of a subject according to claim 16 further including the step of calibrating the head tracking sensor of the head mounted VOG system to the orientation of the subjects canals whereby a transformation matrix can be used to transform movement data to the specific canals.

18. The method for computerized rotational head impulse testing of a subject according to claim 16 wherein the VOG system is operating at least at 250 FPS and wherein the head tracking sensors of the VOG system are 6 degrees of freedom sensors.

19. The method for computerized rotational head impulse testing of a subject according to claim 16 wherein the controlled rotation of the chair includes rotating the chair in an oscillating fashion at low amplitude less than +/−15 degrees and at a frequency between 0.1 and 0.3 Hz.

* * * * *